United States Patent
Ceragioli et al.

(10) Patent No.: US 7,592,482 B2
(45) Date of Patent: Sep. 22, 2009

(54) PROCESS FOR THE PREPARATION OF CONTRAST AGENTS

(75) Inventors: Silvia Ceragioli, Ceriano Laghetto (IT); Giovanni Luca Ciarciello, Ceriano Laghetto (IT); Luciano Castiglia, Milan (IT)

(73) Assignee: Bracco Imaging S.p.A., Milan (IT)

( * ) Notice: Subject to any disclaimer, the term of this patent is extended or adjusted under 35 U.S.C. 154(b) by 5 days.

(21) Appl. No.: 11/991,763

(22) PCT Filed: Aug. 24, 2006

(86) PCT No.: PCT/EP2006/065634

§ 371 (c)(1),
(2), (4) Date: Mar. 10, 2008

(87) PCT Pub. No.: WO2007/031390

PCT Pub. Date: Mar. 22, 2007

(65) Prior Publication Data

US 2009/0118537 A1    May 7, 2009

(30) Foreign Application Priority Data

Sep. 13, 2005  (EP)  .................. 05019852

(51) Int. Cl.
*C07C 229/00* (2006.01)
(52) U.S. Cl. ...................... 562/448; 562/442
(58) Field of Classification Search ............... 562/442, 562/448
See application file for complete search history.

(56) References Cited

FOREIGN PATENT DOCUMENTS

| EP | 0466200 B1 | 4/1996 |
| EP | 0872479 B1 | 9/2002 |
| WO | WO 00/02847 A2 | 1/2000 |
| WO | WO 00/02847 A3 | 1/2000 |

OTHER PUBLICATIONS

PCT Written Opinion of the ISA for PCT/EP2006/065634, mail date Oct. 11, 2006.

*Primary Examiner*—Jafar Parsa
(74) *Attorney, Agent, or Firm*—M. Caragh Noone

(57) ABSTRACT

The present invention refers to a process for preparing a compound of formula (I) through a carboxymethylation reaction occurring in the presence of a suitable alkylating agent and of a base, without the need of monitoring the pH of the reaction environment. The compound of formula (I) is a useful intermediate in the preparation of diagnostic contrast agents for MRI techniques.

15 Claims, No Drawings

PROCESS FOR THE PREPARATION OF CONTRAST AGENTS

This application is the national stage application of corresponding international application number PCT/EP2006/065634 filed Aug. 24, 2006, which claims priority to and the benefit of the European application no. 05019852.2, filed Sep. 13, 2005, all of which are hereby incorporated by reference.

The present invention relates to a process for the preparation of diagnostic contrast agents for magnetic resonance imaging (MRI) and, more in particular, it relates to a process for the preparation of an intermediate compound capable of coordinating a paramagnetic metal ion.

BACKGROUND OF THE INVENTION

MRI is a nuclear magnetic resonance technique that finds application, in the field of diagnostics, to visualize and distinguish between different tissues or organs in the human or animal body through the spatial localization of water protons.

Several MRI contrast agents are known in the art among which is a paramagnetic MRI contrast agent named as gadobenate dimeglumine salt, also referred to as GdBOPTA-Dimeg (MultiHance®, by Bracco Imaging S.p.A).

For a general reference to GdBOPTA-Dimeg see, as an example, EP-A-230893, Invest. Radiol., (1990), 25/Suppl. 1), S59-S60; and C. de Haen et al. Journal of Computer Assisted Tomography 1999, 23 (Suppl. 1):S161-168.

Gadobenate dimeglumine is a paramagnetic MRI contrast agent wherein the paramagnetic gadolinium ion is complexed by BOPTA, a chelating agent forming a highly stable coordinating sphere around the gadolinium ion Gd (III), further salified with N-methylglucamine, this latter also referred to as meglumine.

This MRI contrast agent is characterised, over other known gadolinium complexes, with relaxivity properties that make it particularly advantageous in the field of diagnostics.

It is indicated, as an example, for the detection of focal liver lesions in patients with known or suspected primary liver cancer (e.g. hepatocellular carcinoma) or metastatic diseases.

In addition, it is also indicated for the MRI of the central nervous system in adults, to visualize lesions with abnormal blood brain barrier or abnormal vascularity of the brain, spine and associated tissues.

The ligand coordinating the gadolinium ion, commonly named as BOPTA, is 4-carboxy-5,8,11-tris(carboxymethyl)-1-phenyl-2-oxa-5,8,11-triazamidecan-13-oic acid, having the following formula (I):

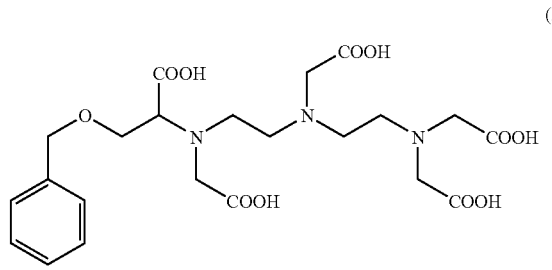

The synthesis of the chelating agent BOPTA of formula (I) may be represented according to the scheme below:

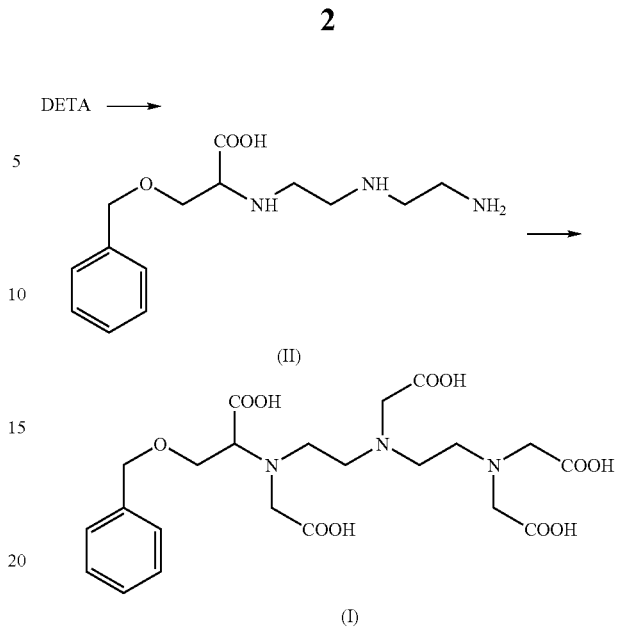

This synthesis comprises, essentially, a selective monoalkylation of diethylenetriamine (DETA) with 2-chloro-3-phenylmethoxy propionic acid, in the presence of water and at a temperature of 50° C., followed by isolation and resin purification of the resulting compound, so as to get N-[2-[(2-aminoethyl)amino]ethyl]-O-(phenylmethyl)serine of formula (II), as the hydrochloride salt.

In the subsequent step, the intermediate (II) is carboxymethylated with bromoacetic acid in water, at a temperature of 50° C. and at pH 10. The resulting crude is then isolated and, after purification through resins, affords the solid compound of formula (I), BOPTA, with a resulting overall yield of 21%.

For a general reference to the above synthetic process and operative conditions thereof see, as an example, EP-A-230893 and Inorg. Chem., 1995, 34(3), 633-42.

According to an improved process, the international patent application WO 00/02847 discloses the preparation of BOPTA from DETA, comprising the alkylation of this latter with 2-chloro-3-(phenylmethoxy)propionic acid potassium salt.

The subsequent carboxymethylation reaction step of the intermediate (II) with bromoacetic acid is carried out at basic pH, and at a temperature of 55° C.

Bromoacetic acid, in particular, is slowly added to the aqueous solution of the precursor of formula (II), for instance present as alkaline carboxylate salt, whilst maintaining the pH values within the range of 11-12 through the addition of a base.

The above operative conditions allow to complete the reaction so as to lead to the compound of formula (I) whilst avoiding an excessive formation of undesired byproducts.

At lower pH levels, in fact, the formation of quaternary ammonium salts may compete with the formation of the desired final compound of formula (I).

On the other side, higher pH values during the carboxymethylation step do require larger amounts of bromoacetic acid due to the competition of hydroxy (OH⁻) groups towards bromine substitution. Furthermore, at higher pH values degradation of the benzyloxypropionic moiety can occur.

By varying the pH conditions, therefore, considerable amounts of by-products may be obtained during the course of the reaction, thus leading to a remarkable decrease in terms of yields of the process and degree of purity of the final compound (I).

Hence, because of the sensitivity of the reaction to pH values, the above carboxymethylation step of WO 00/02847 is carried out by properly dosing the addition of both reactants, that is of bromoacetic acid and of the base, so as to get and maintain the desired basic pH values during the whole course of the reaction.

Typically, on an industrial scale, means are known to suitably dose reactants affecting the pH reaction environment such as, for instance, the use of pH meters.

With the aim of avoiding the formation of the aforementioned byproducts, therefore, pH meters could be used to control and drive the addition of bromoacetic acid and of the base in the above carboxymethylation reaction.

However, as minor variations of pH might lead to the preparation of the final compound in lower yields, because of the formation of relevant amounts of by-products and impurities, any inaccurate electrode pH measurement, whenever used to control the addition of the above reactants, would certainly represent a remarkable drawback and limitation.

In this respect, it would be of utmost importance the need for pH electrodes which provide affordable pH measurements during the whole course of the reaction, under the above operative conditions of temperature and alkalinity.

The above requirement for an accurate and reliable pH measurement of the reaction medium could be even more important in the case of large amounts of sodium ions, for instance due to the use of sodium hydroxide, which presence is known to interfere with pH electrode measurement.

SUMMARY OF THE INVENTION

According to the present invention, it has now been found an improved process for the preparation of BOPTA of formula (I) comprising the carboxymethylation step of the above intermediate of formula (II), without the need of monitoring the pH of the reaction medium and thus dosing the addition of the reactants, up to the completion of the reaction.

It is therefore a first object of the present invention a process for the preparation of the compound of formula (I) according to the scheme below comprising:

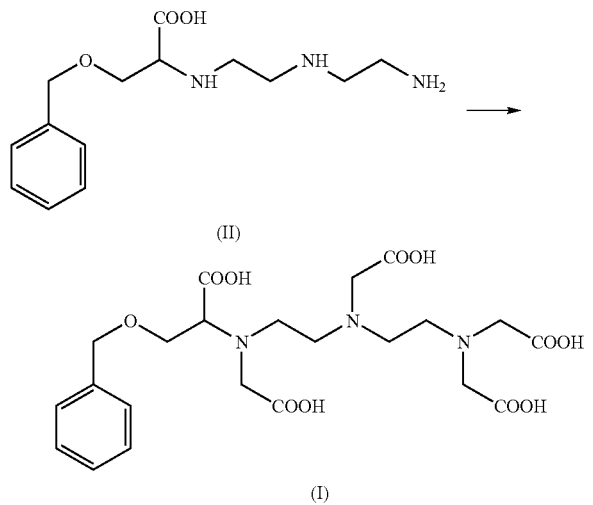

reacting N-[2-[(2-aminoethyl)amino]ethyl]-O-(phenylmethyl)serine of formula (II), or a carboxylate alkaline salt thereof, with a compound of formula (III)

XCH$_2$COOH   (III)

wherein X is a halogen atom, in the presence of a base, characterised in that:

a) in a first step, one or more aliquots of the compound of formula (III) and of the base are added to an aqueous solution of the compound of formula (II), in a simultaneous, consecutive or alternated way of addition, at a temperature ranging from about 10° C. to about 30° C.; and b) in a second step, the reaction mixture is warmed up to a temperature ranging from about 30° C. to about 60° C. and, optionally, one or more aliquots of the compound of formula (III) and of the base are added to the reaction mixture, in a simultaneous, consecutive or alternated way of addition, up to completion of the reaction.

The process of the invention is particularly advantageous for the industrial scale as any of the steps is carried out through a rather simplified and standardized procedure.

In addition, the possibility of operating without the need of continuously monitoring the pH of the reaction during the addition of the compound of formula (III) and of the base, for instance by means of pH electrodes known to lower or potentially lower performances upon usage, is particularly advantageous.

Importantly, the present process allows to obtain the chelating compound of formula (I) in particularly high yields and, also, with a high degree of purity.

DETAILED DESCRIPTION OF THE INVENTION

The preparation of the compound of formula (I) according to the present process is carried out by using a compound of formula (III) wherein X is a halogen atom, in particular a bromine or chlorine atom. Preferably, the compound of formula (III) is bromoacetic acid.

When this latter alkylating agent is employed, aqueous solutions of bromoacetic acid at a concentration of at least 30% by weight are preferably used and, even more preferably, of about 80% by weight.

Typically, the base is selected from the group consisting of alkaline or alkaline-earth metals hydroxides such as, for instance, sodium or potassium hydroxide.

Preferably, the carboxymethylation reaction is carried out in the presence of an aqueous solution of sodium hydroxide. Even more preferably, aqueous solutions of sodium hydroxide at about 30% by weight are employed.

The starting material of formula (II) is known and may be easily prepared according to known methods, for instance as formerly reported through the alkylation of DETA with 2-chloro-3-(phenylmethoxy)propionic acid potassium salt (see, as an example, the aforementioned international patent application WO 00/02847). In this latter case, the aqueous solution of the compound of formula (II) thus obtained may be used as such, in the present process, without the need of being isolated and further purified.

As formerly reported, the carboxymethylation reaction is carried out on an aqueous solution of (II), preferably as a carboxylate alkaline salt and even more preferably as a carboxylate sodium salt.

Unless otherwise provided, within the aqueous solutions of (II) this same compound is present in any suitable concentration. As an example, any suitable concentration is at least of 10% by weight and even more preferably from about 20% to about 50% by weight, which percentage is for instance based and calculated as per WO 00/02847, in terms of trihydrochloride salt.

From the above, it is clear to the skilled person that the concentration of the starting material of formula (II), as well as of any other reactant, is of utmost importance during the scaling up of the present process as it is strictly related to the dimensionability of the plant and, hence, its productivity.

The molar ratio between the compounds of formula (III) and (II), according to the present process, is of at least 4 moles of alkylating compound (III) per mole of substrate (II).

Preferably, the said molar ratio (III):(II) is comprised between 4:1 to 10:1 and, even more preferably, between 7:1 to 9:1.

The amount of base being used in the carboxymethylation reaction is related to the stoichiometry of the reaction and, in particular, to the quantity of alkylating agent of formula (III) being used.

Based on the substrate of formula (II), the said molar ratio may range from about 8 to about 20 moles of base per mole of compound (II).

The process of the invention is characterized by two distinct steps (a) and (b), carried out consecutively.

The first one comprises adding the compound of formula (III) and the base to an aqueous solution of the compound of formula (II), at a temperature ranging from about 10° C. to about 30° C.

The said additions of reactants, in step (a), may comprise a given aliquot or aliquots of compound of formula (III) and a given aliquot or aliquots of base, that can be either added simultaneously, consecutively or alternately, in any order.

Just as an example, if a single aliquot of compound of formula (III) and a single aliquot of base have been added to the aqueous solution of the starting material (II), in step (a), both reactants may be added simultaneously or consecutively in any order, that is compound of formula (III) followed by the base or vice versa.

For ease of reference, such a schedule of addition of both reactants, in step (a), may be represented as follows:

A and B simultaneously; or

A followed by B, or B followed by A, wherein, unless otherwise provided, A stands for the alkylating agent of formula (III) and B stands for the base.

According to an additional example, the compound of formula (III) and the base may be added to the starting material of formula (II), in step (a), through a plurality of additions either occurring simultaneously, consecutively or through an alternate pathway, in any order.

In particular, for instance in the case of four aliquots of the compound of formula (III) and of four aliquots of base to be added, in step (a), any of the schedules below may be followed:

4×A and 4×B simultaneously; or

4×A followed by 4×B, or even 4×B followed by 4×A; or

A alternated by B or B alternated by A, each couple of additions being repeated four times, that is 4×(AB) or 4×(BA), respectively.

Preferably, both reactants of the present process are added, in step (a), through a plurality of additions occurring in an alternate way. Even more preferably, the said additions may comprise from 3 to 8 aliquots of both compound (III) and of base, added in an alternate way [e.g. from 3×(AB) to 8×(AB) or from 3×(BA) to 8×(BA)].

As set forth in the experimental section, possible variations in the schedule of addition of both reactants may also occur including, for instance, an initial alternate addition or additions of A and B followed by a subsequent alternate addition or additions of these same reactants in the reversed order, that is of B and A.

Substantially analogous considerations may apply to step (b), only in the case an additional amount of alkylating agent of formula (III) and of base have to be added to the reaction mixture being obtained from step (a).

Preferably, however, step (b) also comprises that both reactants (III) and the base are added to the reaction mixture as per the above step (a).

Also in this case, both reactants may be either added simultaneously, consecutively or through an alternate way of addition, in any order.

However, whilst the addition of the reactants in step (a) and up to the completion of step (a) itself occurs at a temperature ranging from about 10° C. to about 30° C., step (b) is carried out, during the optional addition of the reactants, and anyway up to completion of the carboxymethylation reaction, at a temperature ranging from about 30° C. to about 60° C.

To this extent, as set forth in the experimental section, the order of the addition of the reactants in step (b), whenever occurring, is independently selected from the order of the addition of the reactants in the previous step (a).

Hence, if step (a) is for instance carried out by adding 5 aliquots of compound (III) and 5 aliquots of base in an alternate way, e.g. as 5×(AB), the optional addition of reactants in step (b), for instance of 3 aliquots of compound (III) and of base in an alternate way, may occur as follows: 3×(AB) or 3×(BA).

According to additional preferred embodiments of the invention, step (a) may be carried out at room temperature, that is at a temperature ranging from about 20° C. to about 25° C., and step (b) may be carried out at a temperature ranging, from about 50° C. to about 55° C., whether or not comprising any addition of the compound of formula (III) and of the base.

Even more preferably, the whole process is performed by operating at temperatures ranging from about 20° C. to about 25° C., in step (a), and from about 50° C. to about 55° C. in step (b).

According to this latter embodiment of the invention, therefore, at the end of the additions of the reactants, in step (a), the reaction medium is warmed up to the temperature of step (b).

From all of the above, it is clear to the skilled person that according to the selected schedule of addition of the reactants in both steps (a) and (b), the total amount of compound of formula (III) and of base to be added may be partitioned among the single additions occurring in any of the steps.

Preferably, though not necessarily, the total amount of compound of formula (III) and of base to be used in the present process is equally partitioned among the single aliquots to be added.

Besides being highly reproducible, the present process is further characterized by a high robustness as possible variations in the time of the addition of the reactants, in any of the steps (a) and (b), do not affect to a significant extent the present process.

Hence, as the carboxymethylation reaction the present process refers to may be completed in a time period suitable for the industrial scale, for instance in a few hours and preferably within 12 hours, it should be clear to the skilled person that the time occurring for the addition of the aliquots of reactant, of any possible pause between the additions themselves and up to completion of the reaction, should be scheduled accordingly.

Typically, on an industrial scale, each addition of reactant is carried out in a time ranging from about one minute to about 60 minutes. Likewise, depending on the number of aliquots of reactants to be added, the time spent between additions—formerly referred to as pause—ma be null or even up to about 45 minutes.

Analogous considerations may also apply to a possible pause occurring between steps (a) and (b), during which time the reaction medium is warmed up to the temperature of step (b), for instance in about 10 to about 30 minutes.

In this respect it is worth noting that the optional addition of the reactants, in step (b), may either start at the time of heating of the reaction mixture, that is just after completion of step (a), or even subsequently, that is after any suitable time period [e.g. possible pause between the last addition of one of the reactants in step (a) and the first optional addition of one of the reactants, in step (b)].

For a general reference to the operative conditions being adopted in the present process, together with details thereof, see the experimental section.

At the completion of the carboxymethylation reaction the mixture is worked up according to conventional methods, for instance as reported in WO 00/02847.

Typically, the reaction mixture is cooled to room temperature (that is from about 20° C. to about 25° C.) and pH is adjusted to about 5 by addition of hydrochloric acid, for instance of a 34% w/w aqueous solution, so as to give an aqueous solution containing the compound of formula (I).

The subsequent purification and recovery of (I) is carried out as reported in WO 00/02847, substantially as follows:

a) percolation and elution on a chromatographic resin;

b) concentration and desalting by nanofiltration;

c) acidification and subsequent crystallization of (I).

The final compound (I) being obtained according to the present process, in its crystalline form, is characterised by a high quality profile and manageability as it is easily centrifugated and dried.

As set forth in the experimental section, several trials have been carried out according to the present process so as to prepare the compound of formula (I).

As reported therein, all of the obtained data clearly support the consistency and reliability of the method despite any of the several variations affecting, for instance, the modality of addition of the alkylating agent and of the base, the amount of the reactants themselves, the range of temperature in steps (a) and (b) and, also, the time of addition of the reactants.

In all of the cases, the compound of formula (I) was obtained in particularly high yields, being calculated from the starting material of formula (II). In addition, this same compound (I) was constantly characterized by a high degree of purity, as per the HPLC data [see % area of (I)] being obtained according to conventional methods.

Unexpectedly, both yields and purity of the compound of formula (I) as obtained according to the present process resulted significantly superior than those obtained in example 1, purposely reported as a comparative example.

According to example 1, in fact, the compound of formula (I) was prepared by first heating the aqueous solution of the starting material (11) at 55° C., by slowly adding the alkylating agent and by suitably dosing the base, so as to keep the desired pH values. Hence, besides the fact that the process of the invention allows to operate on an industrial scale without the need of monitoring the pH of the reaction mixture during the addition of the reactants and the whole course of the reaction, it also provides a remarkable improvement in the synthesis of the intermediate compound of formula (I), to be used in the field of diagnostics.

In addition to all of the above, the present process may also find useful and advantageous applications for any carboxymethylation step occurring on a suitable primary and secondary amine.

Therefore, it is an additional object of the present invention a process for the carboxymethylation of primary or secondary amines so as to lead to the preparation of the compounds of formula (IV) or (V) below

R—N(CH$_2$COOH)$_2$ (IV)

RR'NCH$_2$COOH (V)

which process comprises reacting an aqueous solution of an amine of formula (VI) or (VII)

R—NH$_2$ (VI)

RR'NH (VII)

wherein R and R' represent, each independently, any organic residue susceptible of undergoing a carboxymethylation reaction occurring onto the amino group or groups, with a compound of formula (III)

XCH$_2$COOH (III)

wherein X is a halogen atom, in the presence of a base, characterised in that:

a) in a first step, one or more aliquots of the compound of formula (III) and of the base are added to an aqueous solution of the compound of formula (VI) or (VII), in a simultaneous, consecutive or alternated way of addition, at a temperature ranging from about 10° C. to about 30° C.; and b) in a second step, the reaction mixture is warmed up to a temperature ranging from about 30° C. to about 60° C. and, optionally, one or more aliquots of the compound of formula (III) and of the base are added to the reaction mixture, in a simultaneous, consecutive or alternated way of addition, up to completion of the reaction.

Unless otherwise provided, any of the R and R' group may represent any optionally substituted straight or branched hydrocarbon chain susceptible of being carboxymethylated at the amino group or groups. In particular, the said R and R' groups should sustain the action of the reactants under the above operative conditions so as to yield the compounds of formula (IV) or (V), without the formation of significant amounts of by-products.

For any additional consideration about the carboxymethylation of primary or secondary amines and possible variations thereof, including the amount of reactants and modality of their addition in any of the steps (a) and (b), see any of the previous comments extensively provided for the preparation of the compound of formula (I).

With the aim of better illustrate the present invention, without posing any limitation to it, the following examples are herewith provided.

EXAMPLE 1

Preparation of the Compound of Formula (I): 4-carboxy-5,8,11-tris(carboxymethyl)-1-phenyl-2-oxa-5,8,11-triazamidecan-13-oic Acid (I).

Comparative Example

The title compound was prepared by working in analogy to what disclosed in the aforementioned WO 00/02847 (see example 5 of the same).

452 g of an aqueous solution of the carboxylate sodium salt of (II) (37% w/w as trihydrochloride and corresponding to 0.43 mol) were charged in a vessel of 3 L with 92 ml of water. The solution was heated to 55° C. and reacted with 536 g of an 80% bromoacetic acid aqueous solution, being slowly added. pH was kept at 11-12 with a 30% (w/w) sodium hydroxide solution. The reaction was completed in about 5 hours at 55° C. and pH 11-12.

The solution was then cooled to 25° C. and pH was adjusted to about 5.5 with a 34% hydrochloric acid solution (w/w) so as to lead to an aqueous solution of the title compound.

Titre HPLC Area %: 63 (BOPTA content)
Yield: 66% in solution based on compound (II).

EXAMPLE 2

Preparation of 4-carboxy-5,8,11-tris(carboxymethyl)-1-phenyl-2-oxa-5,8,11-triazamidecan-13-oic Acid (I) According to Alternate Sequential Additions of the Reactants Step (a) In a vessel of 3 L, 417 g of an aqueous solution of the carboxylate sodium salt of (II) (40% w/w as trihydrochloride and corresponding to 0.43 mol), kept at room temperature (20°-25° C.), was reacted with 74 g (0.43 mol) of an 80% bromoacetic acid aqueous solution, which was added in 15 minutes. At the end of the addition, 114 g of a 30% aqueous solution of sodium hydroxide (0.85 mol, solution at 30%) was added in 15 minutes, maintaining this same temperature of 20-25° C.

Then, three additional aliquots of an 80% bromoacetic acid solution (74 g each aliquot) and three additional aliquots of a 30% sodium hydroxide solution (114 g each aliquot) were consecutively added, in an alternated way, to the reaction mixture. Each addition was carried out in 15 minutes.

Step (b) Then, at the end of step (a), it was started either the addition of aliquots of sodium hydroxide and of bromoacetic acid as set forth below and, also, the warming up of the reaction mixture up to a temperature comprised between 50-55° C. Warming of the reaction mixture occurred in about 30 minutes.

Through additions of sodium hydroxide followed by additions of bromoacetic acid, four aliquots of a 30% sodium hydroxide solution (114 g each aliquot) and four aliquots of an 80% bromoacetic acid solution (74 g each aliquot) were added to the reaction mixture, in an alternate way. Each addition was carried out in 15 minutes.

At the end of the addition of the reactants, the solution was maintained at a temperature comprised between about 50° C. to about 55° C. for 3 hours. Then, it was cooled to room temperature and pH was adjusted to about 5.5, with a 34% hydrochloric acid solution (w/w) so as to lead to an aqueous solution of the title compound.

Titre HPLC Area %: 70 (BOPTA content)
Yield: 76% in solution based on compound (II)

EXAMPLE 3

Preparation of the Compound of Formula (I) Through Different Embodiments of the Process The compound of formula (I) was prepared according to the present process, by properly varying some of the operative conditions being reported in example 2 such as: temperature, sequence of addition of the aliquots of reactants, amount of the reactant themselves and time of addition.

Trials from 1 to 2 and 4 to 6 were performed by using 417 g of an aqueous solution of the carboxylate sodium salt of (II) (40% w/w as trihydrochloride and corresponding to 0.43 mol). Trial 3 was carried out by using and aqueous solution of the carboxylate sodium salt of (II) at 34% w/w, calculated as trihydrochloride salt, and corresponding to 0.43 mol.

In all of the trials there were added aliquots of an 80% w/w bromoacetic acid solution and a 30% w/w sodium hydroxide solution. Results are reported in the following table I In every trial:
A corresponds to an 80% bromoacetic acid solution (74 g; 0.43 mol);
A' corresponds to half the amount of A (37 g; 0.213 mol);
B corresponds to a 30% sodium hydroxide solution (114 g; 0.85 mol);
B' corresponds to half the amount of B (57 g; 0.425 mol);
B" corresponds to a 30% sodium hydroxide solution (89 g; 0.65 mol).

The time to bring the reaction mixture from the temperature of step (a) to the temperature of step (b) is of about 30 minutes. Any addition of reactants, in step (b), either started just upon completion of step (a), that is at the time of heating, or subsequently as per the selected time pause.

TABLE I

| | Step (a) | Step (b) | Time Addition Pause Completion | Area HPLC (%) | Yields (%) |
|---|---|---|---|---|---|
| 1 | 20-25° C. 4 × (AB) | 50-55° C. 4 × (BA) | Additions: 15 min<br>Pause: 0 betw consecutive additions of A and B or of B and A or of any consecutive additions of (AB) or of (BA) and betw steps (a) and (b)<br>Completion: 3 hr | 70 | 76 |
| 2 | 20-25° C.<br>i) 3 × (AB)<br>ii) 1 × (AB) | 50-55° C.<br>i) 1 × (AB)<br>ii) 3 × (BA) | Additions: 15 min<br>Pause: 0 betw consecutive additions of A and B or of B and A, in both steps (a) and (b); 0 betw consecutive additions (i) of (AB) in step (a); 30 min betw (i) and (ii) in step (a); 30 min betw steps (a) and (b); 30 min betw (i) and (ii) in step (b); 30 min betw consecutive additions (ii) of (BA) in step (b)<br>Completion: 3 hr | 73 | 79 |
| 3* | 10-25° C.<br>4 + (AB) | 50-55° C.<br>i) AB,<br>ii) 2 × (BA),<br>iii) AB, | Additions: 30 min<br>Pause: 0 betw consecutive additions of A and B or of B and A or of consecutive additions of (AB) or of (BA) in step (a) and (i) and (ii) of step (b); 60 min betw A and B in (iii) in step (b); 0 | 72 | 78 |

TABLE I-continued

| Step (a) | Step (b) | Time Addition Pause Completion | Area HPLC (%) | Yields (%) |
|---|---|---|---|---|
| | iv) B" | betw steps (a) and (b); 0 betw (i) and (ii), (ii) and (iii), and (iii) and (iv) in step (b); Completion: 1 hr | | |
| 4   20-25° C. 8 × (A'B') | 50-55° C. 8 × (A'B') | Additions: 15 min Pause: 0 betw consecutive additions of A' and B' or of consecutive additions of (A'B') in both steps (a) and (b); 0 betw steps (a) and (b) Completion: 15 min | 73 | 79 |
| 5   15-25° C. 4A + 4B simultaneously | 50-55° C. 2A + 2B simultaneously | Additions: 1 hr in step (a) and 1 hr in step (b) Pause: 30 mm betw steps (a) and (b) Completion: 5 hr | 70 | 76 |
| 6   20-25° C. i) 4 × (AB) ii) 4 × (BA) | 50-55° C. — | Additions: 15 min Pause: 0 betw consecutive additions of A and B or of B and A; 30 min betw consecutive additions of (AB) or of (BA) and between (i) and (ii) Completion: 3 hr | 71 | 77 |

The data reported in table I clearly support any of the aforementioned advantages of the present process and, also, the robustness of the method itself together with its reproducibility and reliability upon variations of the adopted operative conditions.

In particular, trial (1) corresponds to previous example 2, which unexpected results in terms of yield and purity of (I) over known prior art methods have been already reported.

Moreover, the possibility of varying the time of addition of the reactants, the sequence and modality of the additions themselves and, also, the possibility of varying to a rather great extent the amount of reactants to be added, despite the sensitivity of the reaction itself to possible pH variations, is certainly to be regarded as unexpectedly advantageous.

This latter aspect is further supported by a comparison between trials 1 and 3, both leading to comparable results in terms of (I) despite the fact that the total amount of base is as twice the total amount of alkylating agent in trial 1 and the corresponding total amount of base exceeds to a rather great extent (by B") twice the total amount of alkylating agent in trial 3.

EXAMPLE 4

Preparation of the Compound of Formula (I) by Varying the Range of Temperature in Steps (a) and (b).

The compound of formula (I) was prepared as reported in example 3 by adding bromoacetic acid and the base according to the following schedule: (i) 3×(AB) and (ii) 1×(AB) in step (a); and (i) 1×(AB) and (ii) 3×(BA) in step (b), and by following the time schedule of trial 2 (example 3).

By working in this way, the compound of formula (I) was prepared as per the trials below by varying the range of temperature in steps (a) and (b).

Results are reported in table II below

TABLE II

| | Temperature ° C. Step (a) | Temperature ° C. Step (b) | Compound (I)- BOPTA Area % |
|---|---|---|---|
| 1 | 20-25 | 50-55 | 73 |
| 2 | 20-25 | 40-45 | 72 |
| 3 | 20-25 | 58-62 | 70 |
| 4 | 10-15 | 39-42 | 73 |

Trial (1) of table (II) corresponds to trial (2) of table I (see example 3). As set forth in table II, possible variations in the range of temperature of both steps (a) and (b), within the ranges formerly specified according to the present process, constantly provide for a final compound of formula (I) with a substantially high degree of purity, as expressed in terms of HPLC % area.

The invention claimed is:

1. A process for the preparation of the compound of formula (I) according to the scheme below comprising:

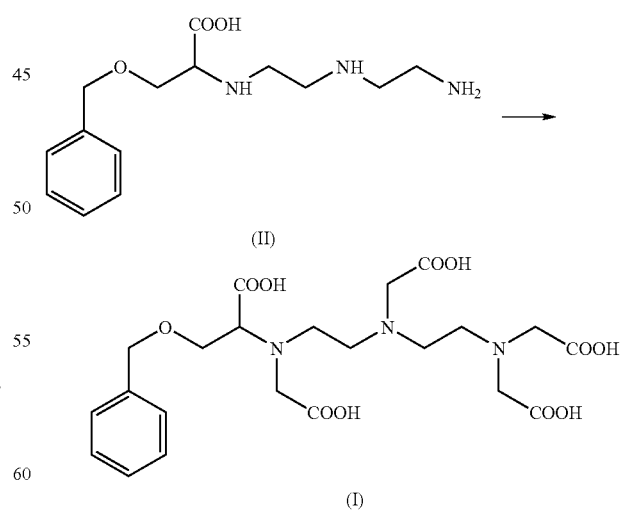

reacting N-[2-[(2-aminoethyl)amino]ethyl]-O-(phenylmethyl)serine of formula (II), or a carboxylate alkaline salt thereof, with a compound of formula (III)

XCH$_2$COOH   (III)

wherein X is a halogen atom, in the presence of a base, characterised in that:
- a) in a first step, one or more aliquots of the compound of formula (III) and of the base are added to an aqueous solution of the compound of formula (II), simultaneously, consecutively or alternately, at a temperature ranging from 10° C. to 30° C.; and
- b) in a second step, the reaction mixture is warmed up to a temperature ranging from 30° C. to 60° C. and, optionally, one or more aliquots of the compound of formula (III) and of the base are added to the reaction mixture, simultaneously, consecutively or alternately, up to completion of the reaction.

2. The process according to claim 1 wherein X, within the compound of formula (III), is a chlorine or bromine atom.

3. A process according to claim 2 wherein the compound of formula (III) is bromoacetic acid.

4. A process according to claim 1 wherein the base is selected from the group consisting of alkaline or alkaline-earth metals hydroxides.

5. A process according to claim 4 wherein the base is sodium hydroxide.

6. A process according to claim 1 wherein the compound of formula (II) is present as carboxylate sodium salt.

7. A process according to claim 1 wherein the compound of formula (II) is obtained by alkylating diethylentriamine with 2-chloro-3-(phenylmethoxy)propionic acid potassium salt.

8. A process according to claim 1 wherein, in step (a), from 1 to 8 aliquots of compound of formula (III) and from 1 to 8 aliquots of base are added to an aqueous solution of the compound of formula (II), in a simultaneous, consecutive or alternated way of addition.

9. A process according to claim 8 wherein, in step (a), from 3 to 8 aliquots of compound of formula (III) and from 3 to 8 aliquots of base are added to an aqueous solution of the compound of formula (II), in a simultaneous, consecutive or alternated way of addition.

10. A process according to claim 1 wherein, in step (b), one or more aliquots of the compound of formula (III) and of the base are added to the reaction mixture, in a simultaneous, consecutive or alternated way of addition.

11. A process according to claim 10 wherein, in step (b), from 1 to 8 aliquots of compound of formula (III) and from 1 to 8 aliquots of base are added to the reaction mixture, in a simultaneous, consecutive or alternated way of addition.

12. A process according to claim 1 wherein step (a) is carried out at a temperature ranging from 20° C. to 25° C.

13. A process according to claim 1 wherein step (b) is carried out at a temperature ranging from 50° C. to 55° C.

14. A process according to claim 1 wherein step (a) is carried out at a temperature ranging from 20° C. to 25° C., and step (b) is carried out at a temperature ranging from 50° C. to 55° C.

15. A process according to any one of the previous claims wherein the reaction mixture from step (b) is cooled at room temperature and acidified to give an aqueous solution of the compound of formula (I).

* * * * *